United States Patent

Burke et al.

Patent Number: 5,874,641
Date of Patent: Feb. 23, 1999

[54] PROCESS TO PREPARE A TERMINAL ALDEHYDE

[75] Inventors: Patrick M. Burke; James M. Garner, both of Wilmington, Del.; Wilson Tam, Boothwyn, Pa.; Kristina A. Kreutzer, Wilmington, Del.; Antonius J.J.M. Teunissen, Geleen, Netherlands; Carina S. Snijder; Carolina B. Hansen, both of Sittard, Netherlands

[73] Assignees: DSM N.V., Heerlen, Netherlands; E. I. du Pont de Nemours and Company, Wilmington, Del.

[21] Appl. No.: 844,104

[22] Filed: Apr. 28, 1997

Related U.S. Application Data

[60] Continuation-in-part of Ser. No. 801,920, Feb. 14, 1997, abandoned, which is a division of Ser. No. 616,721, Mar. 15, 1996, abandoned.

[51] Int. Cl.$^6$ .................................................. C07C 45/50
[52] U.S. Cl. ........................ 568/454; 568/451; 502/155
[58] Field of Search .................... 502/155, 158, 502/162; 568/454, 451

[56] References Cited

U.S. PATENT DOCUMENTS

| | | | |
|---|---|---|---|
| 4,769,498 | 9/1988 | Billig et al. | 568/454 |
| 4,885,401 | 12/1989 | Billig | 568/454 |
| 5,210,260 | 5/1993 | Bohshar et al. | 558/90 |
| 5,235,113 | 8/1993 | Sato | 568/454 |

*Primary Examiner*—Gary Geist
*Assistant Examiner*—Sreeni Padmanabhan
*Attorney, Agent, or Firm*—Pillsbury Madison & Sutro LLP

[57] ABSTRACT

A hydroformylation catalyst composition comprising iridium or rhodium and a bidentate organic phosphite ligand wherein the two phosphorus atoms of the phopshite ligand are linked with a 2,2'-dihydroxyl-1,1'-binapthalene bridging group having the following structure (Q):

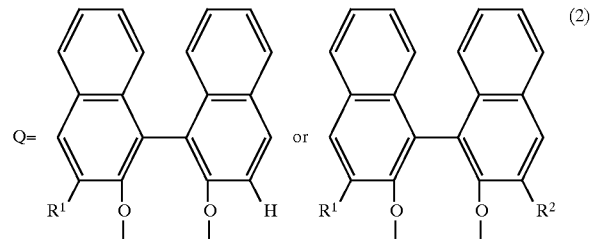

in which $R^1$ and $R^2$ are substituents other than hydrogen.

8 Claims, No Drawings

PROCESS TO PREPARE A TERMINAL ALDEHYDE

RELATED APPLICATIONS

This is a continuation-in-part application of parent application Ser. No. 08/801,920 filed Feb. 14, 1997 abandoned, which was a divisional application of application Ser. No. 08/616,721 filed Mar. 15, 1996 abandoned, the complete disclosures of which is incorporated herein by reference.

FIELD OF THE INVENTION

The invention relates to a process for the preparation of a terminal aldehyde by hydroformylation by reacting an ethylenically unsaturated organic compound with carbon monoxide and hydrogen in the presence of a catalyst system comprising iridium or rhodium and a bidentate organic phosphite ligand.

BACKGROUND OF THE INVENTION

Bidentate organic phosphite ligands are characterized in that two phosphorus atoms are present in the molecule and in that one organic group (the bridging group) is bonded with both phosphorus atoms. The bidentate phosphite ligand is furthermore characterized in that each trivalent phosphorus atom is further bonded with two other monovalent organic groups or with one divalent organic group.

U.S. Pat. No. 5,235,113 describes a hydroformylation process in which a bidentate organic phosphite ligand is used in a homogeneous hydroformylation catalyst system also comprising rhodium. This patent describes a process for preparing aldehydes by hydroformylation of alkenically unsaturated organic compounds, for example 1-octene or dimerized butene, using the above catalyst system. A disadvantage of the process according to U.S. Pat. No. 5,235,113 is that the selectivity to terminal organic aldehyde compounds when starting from internally ethylenically unsaturated functional organic compounds is generally too low for a commercially attractive process. However, with some of the disclosed multidentate phosphites of U.S. Pat. No. 5,235,113, such as tetrakis(di-(2,4-di-tert-butylphenyl) phosphito)-pentaerythritol, reasonable selectivities to terminal aldehydes are achieved. A drawback of the use of these "high selectivity" ligands is that the hydroformylation activity of the catalyst system is also too low for a commercially attractive process. Increasing the catalyst activity of these catalyst systems by increasing the temperature is not possible because the ligands are thermally unstable at higher temperatures. In addition, selectivity decreases at higher temperature, because the rate of competing olefin hydrogenation reactions increases with temperature more rapidly than the rate of the hydroformylation reaction. Hydroformylation processes involving organic bidentate ligands containing two trivalent phosphorus atoms, in which the two phosphorus atoms are linked with a 2,2'-dihydroxyl-1,1'-binaphthalene bridging group, are described in the above mentioned U.S. Pat. No. 5,235,113 and in EP-B-214622, EP-A-353770, WO-A-9303839 and EP-A-556681. EP-B-213639 describes on page 38 a compound with methyl substituents on both the 3 and 3' positions of a 2,2'-dihydroxyl-1,1'-binaphthalene bridging group. However, no indication is given that the use of this class of ligands having such a bridging group would give favorable results in terms of terminal aldehyde selectivity and catalyst activity when starting from unsaturated organic compounds and especially when starting from internally unsaturated organic compounds.

WO-A-9518089 describes a process for preparing 5-formylvalerate ester starting from an internally unsaturated 3-pentenoate ester using a catalyst system comprising rhodium and a bidentate phosphite ligand, for example tetrakis(di-(2,4-di-tert-butylphenyl)phosphito) pentaerythritol.

SUMMARY OF THE INVENTION

Thus, this invention provides a process for the preparation of a terminal aldehyde by hydroformylation by reacting an ethylenically unsaturated organic compound with carbon monoxide and hydrogen in the presence of a catalyst system comprising iridium or rhodium and a bidentate organic phosphite ligand having the structure:

characterized in that the two phosphorus atoms of the phosphite ligand are linked with a 2,2'-dihydroxyl-1,1'-binapthalene bridging group having the following structure (Q):

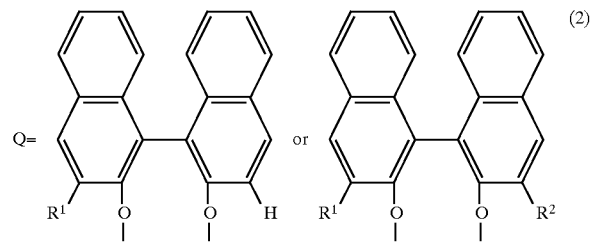

in which $R^1$ and $R^2$ are substituents other than hydrogen and in which $R^3$ and $R^4$ are the same or different substituted monovalent aryl groups and/or any one of $OR^3$ and $OR^4$ connected to one phosphorus atom forms an —O—$R^5$—O—group, where $R^5$ is a divalent organic group containing one or two aryl groups.

The aim of this invention is to provide a process for the preparation of terminal aldehydes with high catalyst performance (selectivity and/or activity). When the process according the invention is used, high selectivities to terminal aldehyde compounds are achieved, combined with a relatively high catalyst activity. The advantages of this novel process are even more pronounced when starting from internally unsaturated organic compounds. Preparing terminal aldehydes starting from internally unsaturated compounds using previously known hydroformylation processes generally results in lower selectivity to terminal aldehydes, more hydrogenation of the olefinic double bond and/or lower catalytic activity. An additional advantage of the process according to this invention is that the linearity (linear aldehydes/(linear+branched aldehydes)) is high. This is advantageous because it facilitates the isolation of the desired terminal aldehyde from a mixture of terminal and branched aldehydes.

DETAILED DESCRIPTION OF THE INVENTION

The advantages of the present process are achieved using a ligand represented by the structure:

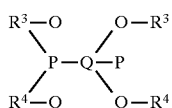

wherein the two phosphorus atoms of the phopshite ligand are linked with a 2,2'-dihydroxyl-1,1'-binapthalene bridging group having the following structure (Q):

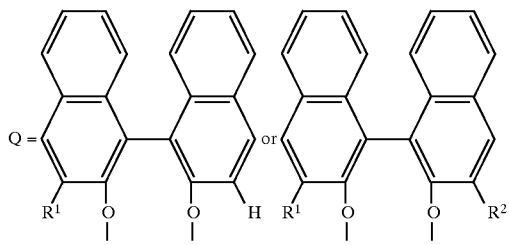

in which $R^1$ and $R^2$ are substituents other than hydrogen and in which $R^3$ and $R^4$ are the same or different substituted monovalent aryl groups and/or any one of $OR^3$ and $OR^4$ connected to one phosphorus atom forms an —O—$R^5$—O—group, where $R^5$ is a divalent organic group containing one or two aryl groups.

The substituents $R^1$ and $R^2$ are preferably organic groups containing at least one carbon atom, and more preferably containing 1 to 20 carbon atoms.

Preferably $R^1$ and $R^2$ are individually selected from the group of alkyl, aryl, triarylsilyl, trialkylsilyl, carboalkoxy, carboaryloxy, aryloxy, alkoxy, alkylcarbonyl, arylcarbonyl, oxazole, amide, amine or a nitrile.

For $R^1$ and $R^2$, the alkyl group is preferably a $C_1$–$C_{10}$ alkyl group, for example methyl, ethyl, propyl, isopropyl, butyl, tert-butyl, isobutyl, pentyl or hexyl. An example of a suitable triarylsilyl group is triphenylsilyl and examples of a suitable trialkylsilyl group are trimethylsilyl and triethylsilyl. Preferred aryl groups have 6 to 20 carbon atoms such as, for example, phenyl, benzyl, tolyl, naphthyl, anthranyl or phenanthryl. Preferred aryloxy groups have 6 to 12 carbon atoms such as, for example, phenoxy. Preferred alkoxy groups have 1 to 20 carbon atoms such as, for example methoxy, ethyoxy, tert-butoxy or isopropoxy. Preferred alkylcarbonyl groups have 2 to 12 carbon atoms, for example methylcarbonyl, tert-butylcarbonyl. Preferred arylcarbonyl groups have 7 to 13 carbon atoms, for example phenylcarbonyl. Preferred amide groups contain a $C_1$–$C_4$ alkyl group and preferred amide groups contain two $C_1$–$C_5$ alkyl groups.

Most preferably, $R^1$ and $R^2$ are individually a carboalkoxyl or a carboaryloxy group, —$CO_2R$, in which R is a $C_1$–$C_{20}$ alkyl group or a $C_6$–$C_{12}$ aryl group and preferably a $C_1$–$C_8$ alkyl group. Examples of suitable R-groups are methyl, ethyl, propyl, isopropyl, n-butyl, tert-butyl, isobutyl, phenyl and tolyl. Even more preferably both $R^1$ and $R^2$ are the same carboaryloxy and more preferably the same carboalkoxyl group because the resulting ligands are more easily obtainable.

The 2,2'-dihydroxyl-1,1'-binaphthalene bridging group can optionally be further substituted with other groups, for example halogen, for example, Cl or F, or one of the substituents $R^1$ which may be present on the bridging group Q as described above.

$R^3$ and $R^4$ are the same or different monovalent aryl groups, preferably groups with 6 to 20 carbon atoms. It is to be understood that all four $R^3$ and $R^4$ groups can be different. Preferably all four groups are the same because the resulting ligands are more readily available. Alternatively $OR^3$ and $OR^4$ (connected to the same P-atom) can form an —O—$R^5$—O—group where $R^5$ is a divalent group of 6 to 40 carbon atoms containing one or two aryl groups. Preferably $R^3$ and $R^4$ are monovalent aryl groups, for example phenyl, containing at least one group, $R^6$, other than hydrogen in an ortho position relative to the oxygen atom, where $R^6$ is a $C_1$ to $C_{20}$ alkyl or $C_6$–$C_{20}$ aryl group and preferably a $C_1$–$C_6$ alkyl group. Other preferred monovalent aryl groups for $R^3$ and $R^4$ are monovalent fused aromatic ring systems with 2 or more rings having 10–20 carbon atoms. $R^3$ and $R^4$ can optionally be further substituted with for example $C_1$–$C_{10}$ alkyl, $C_6$–$C_{20}$ aryl, $C_1$–$C_{10}$ akoxy or $C_6$–$C_{20}$ aryloxy groups or halogen groups, for example F, Cl or Br or amine groups.

When the aryl groups $R^3$ and $R^4$ are substituted with at least one $R^6$-group in the ortho-position relative to the phenolic oxygen atom, higher linear selectivity is observed using these ligands in a hydroformylation process. Examples of these $R^6$ groups are methyl, ethyl, propyl, isopropyl, isobutyl, tert-butyl or n-butyl. For $R^6$ preferably only one bulky group, having a steric hinderance of isopropyl or greater, is ortho-substituted on the aryl group. When less bulky substituents are used preferably both ortho positions are substituted with these groups. The preferred $R^6$-substituted aryl group for $R^3$ and $R^4$ is 2-isopropylphenyl or 2-tert-butylphenyl group.

Another preferred class of aryl groups for $R^3$ and $R^4$ are fused aromatic ring systems having 2 or more fused rings. The number of fused rings can be, for instance, 2 to 4 rings. The fused ring systems having 2 or more rings can have 10 to 20 carbon atoms. The fused ring systems do not necessarily have to be substituted at the ortho position (on the carbon atom adjacent to the carbon atom which is bonded to the oxygen atom in formula (1)) with groups other than hydrogen. It has been found that when $R^3$ and/or $R^4$ is such an unsubstituted aromatic ring system, high catalyst activity, a high selectivity to terminal aldehyde and a high linearity can be achieved. Examples of such fused aromatic ring systems are phenanthryl, anthryl and naphthyl groups. Preferably 9-phenanthryl or 1-naphthyl groups are used. The aromatic ring systems can optionally be substituted with for example the earlier mentioned substituents, for example on the other positions of the ring systems, not being the above described ortho position.

Examples where $R^3$ and $R^4$ are linked to form divalent groups $R^5$ are $C_6$–$C_{25}$ diaryl groups, for example a binaphthol or biphenol group, according to the following formulas:

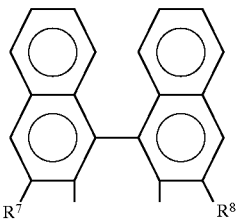

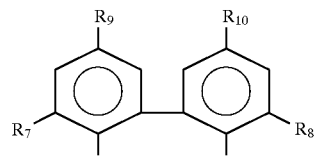

in which preferably $R^7$ and $R^8$ are H or alkyl groups. Examples of $R^7$ and $R^8$ are H, isopropyl, isobutyl, tert-butyl, or one of the substituents $R^1$ which may be present on the bridging group Q described above. $R^9$ and $R^{10}$ may be hydrogen, hydrocarbyl, or alkoxy groups.

Examples of phosphite ligands which can be used in the process according to this invention are shown below. The ligand number as shown below corresponds with the references to the ligands used in the examples. In the formulas shown below the following fragments correspond to:
-=methyl,
_/=ethyl,
Ph=phenyl,
-<=isopropyl,
Me=methyl,
+=tert-butyl.

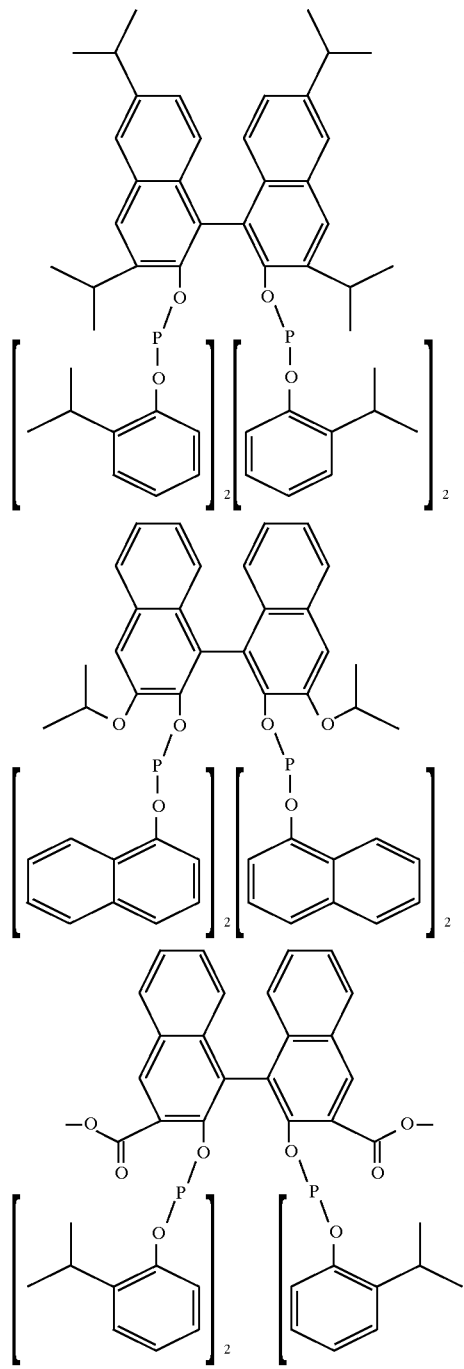

Ligand 1

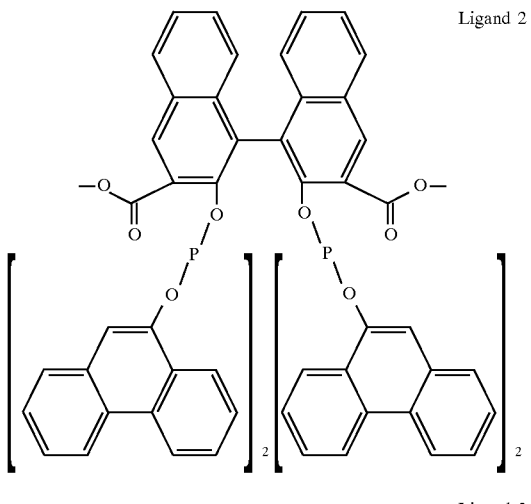

Ligand 2

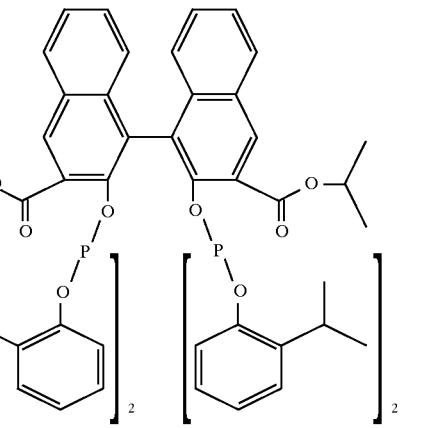

Ligand 3

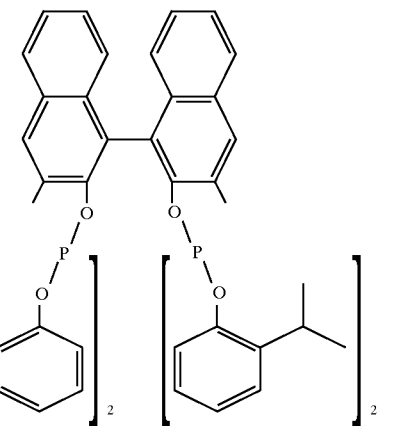

Ligand 4

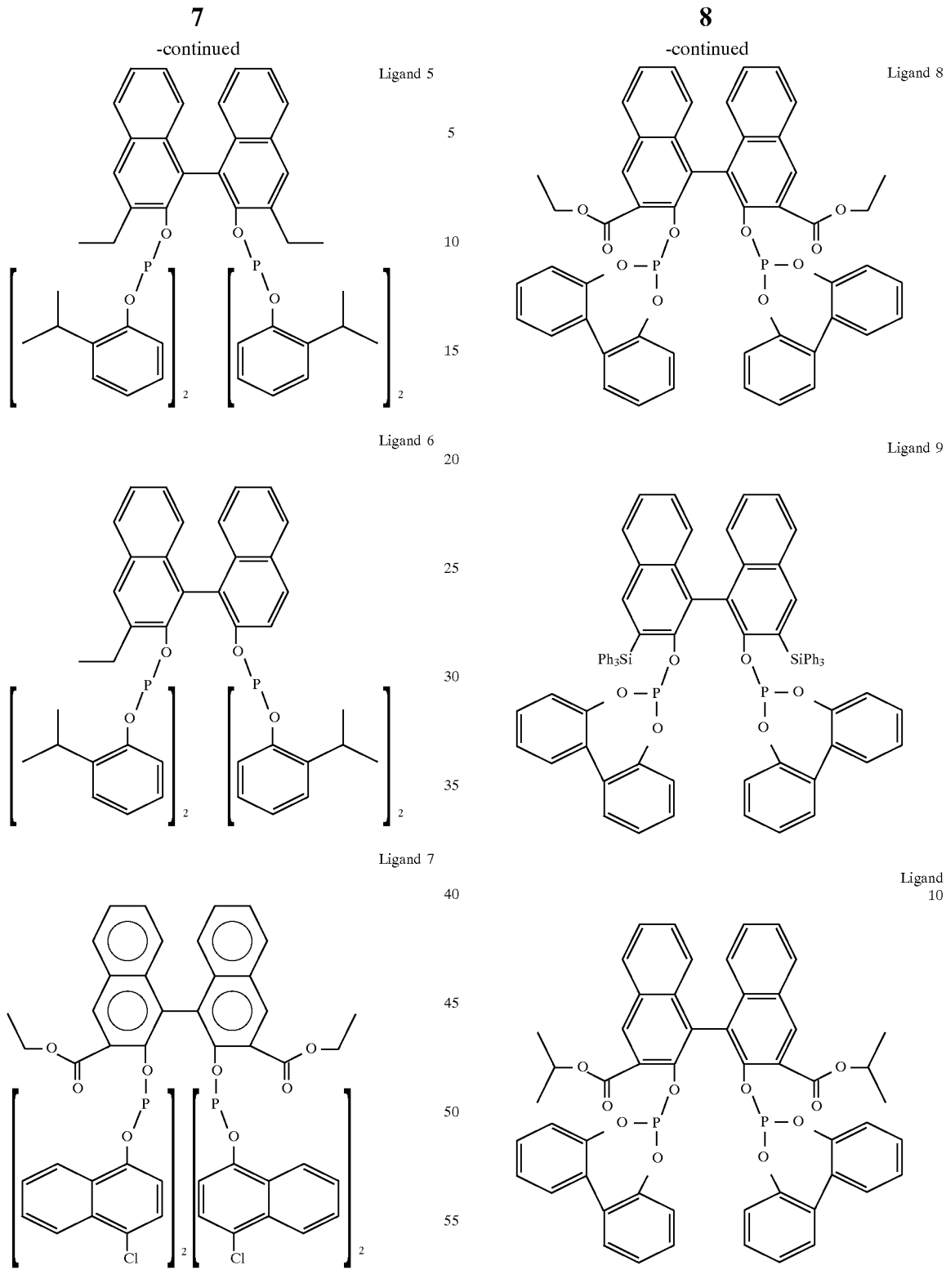

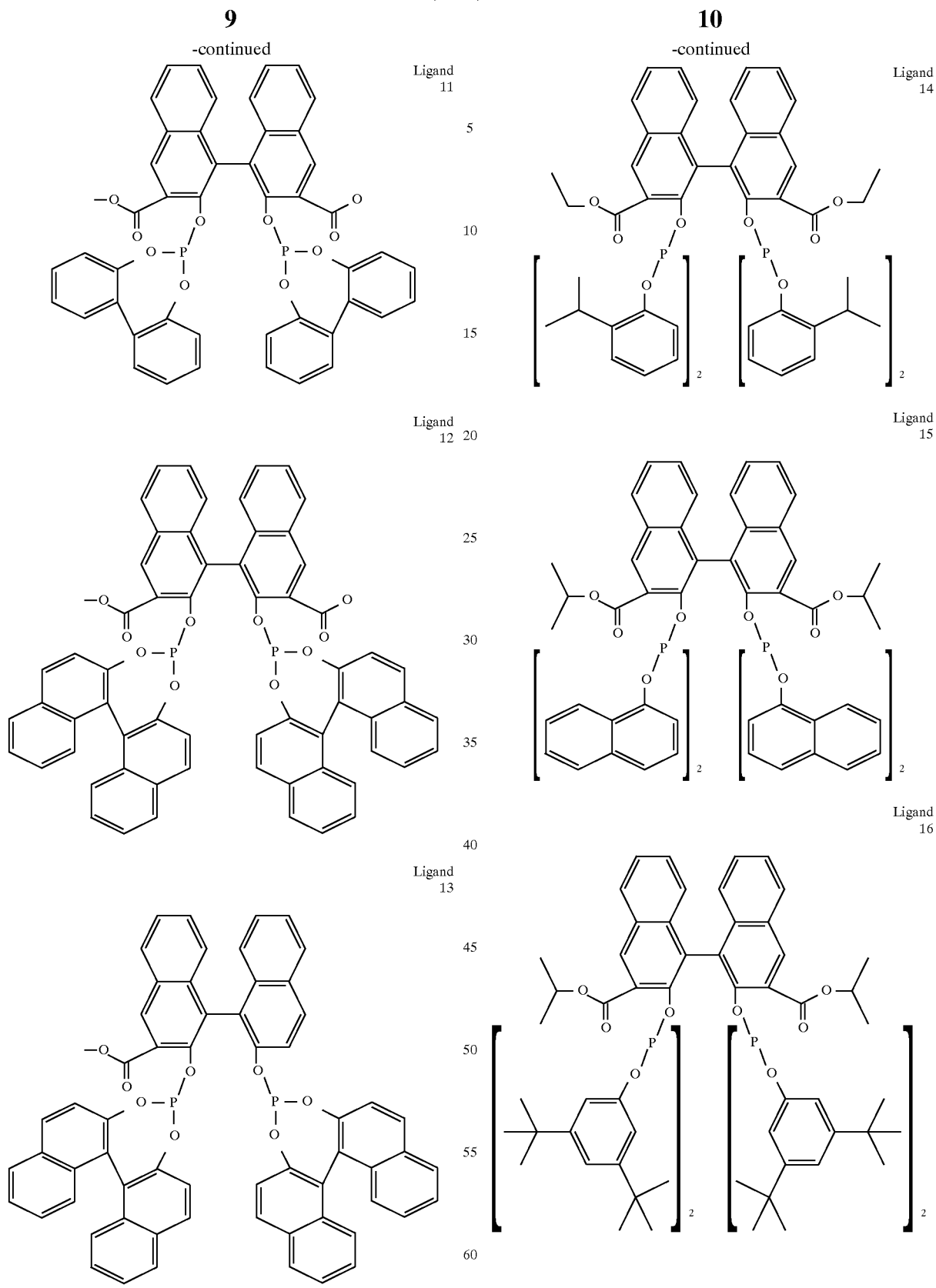

Ligand 17
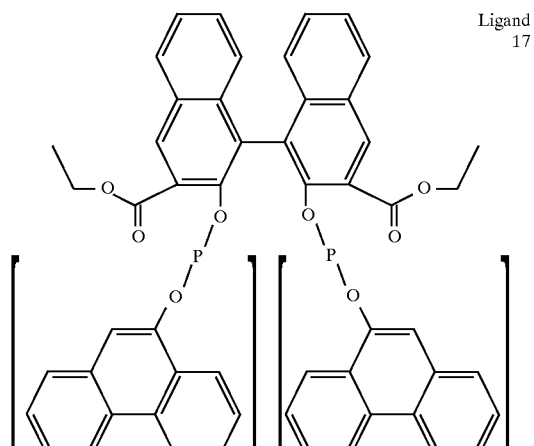
Ligand 20
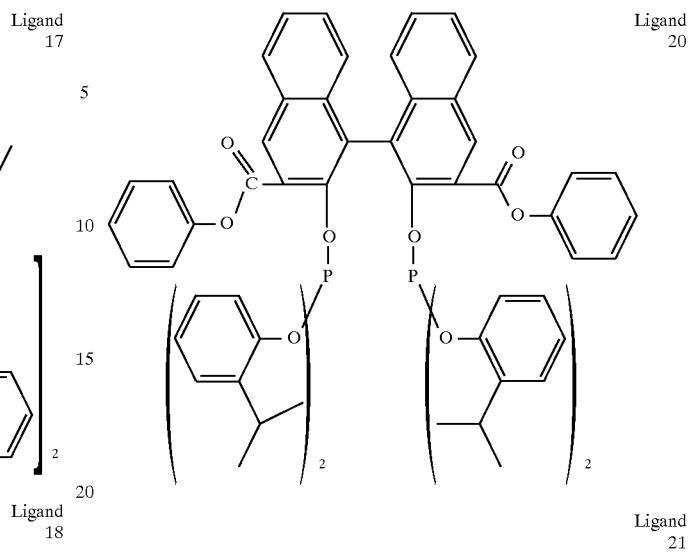
Ligand 18
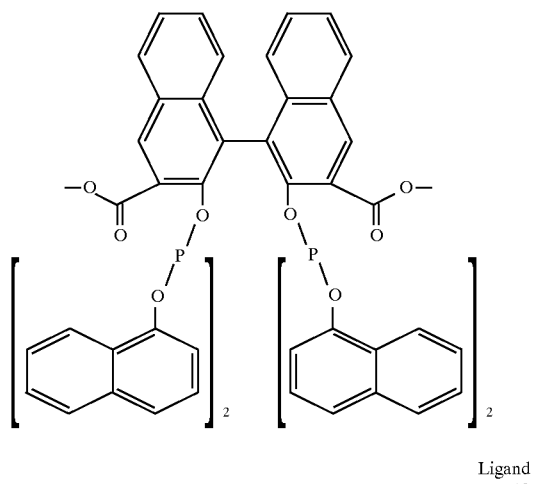
Ligand 21
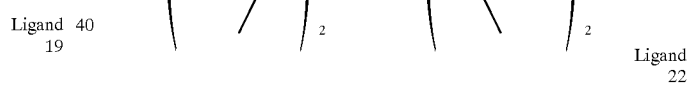
Ligand 19
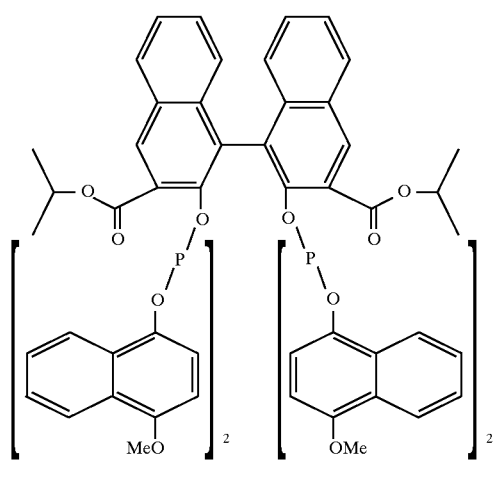
Ligand 22
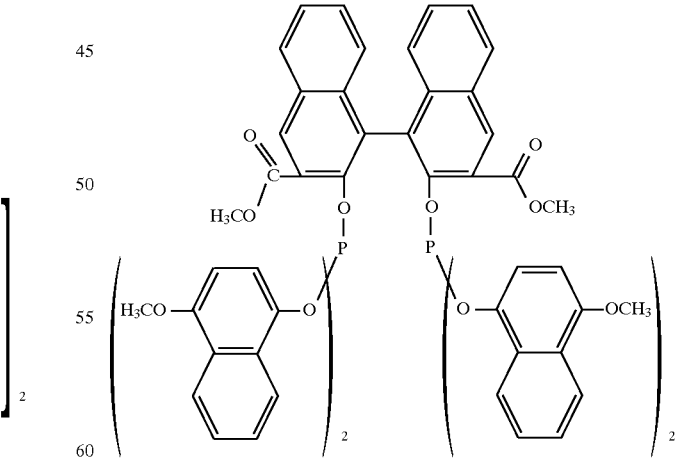

-continued
Ligand 23
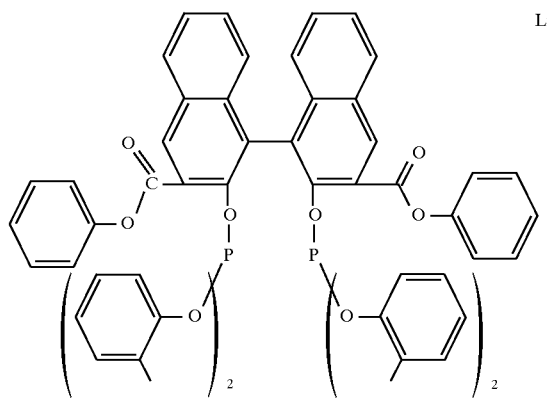
Ligand 24
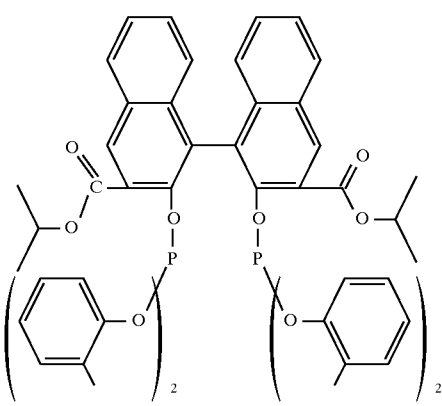
Ligand 25
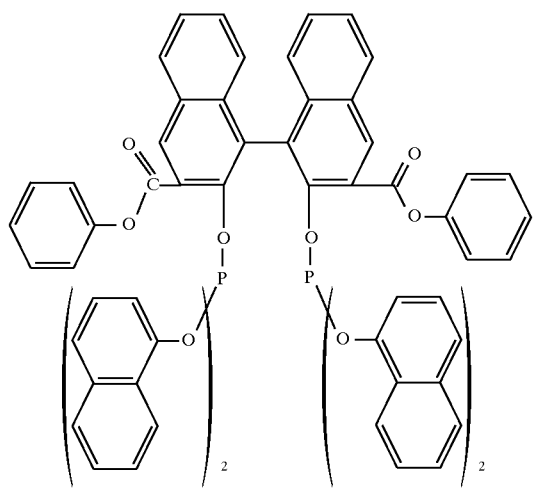
Ligand 26
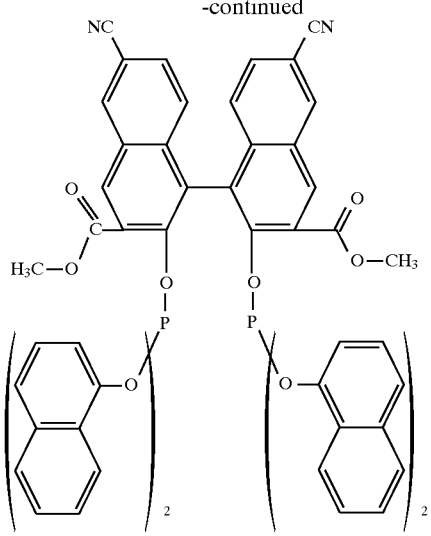
Ligand 27
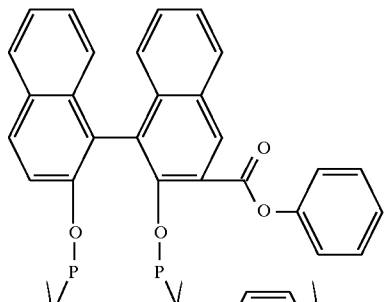
Ligand 28
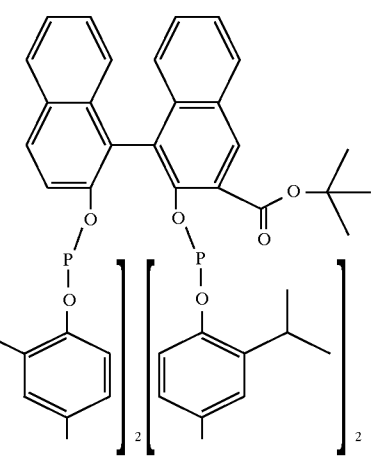

These ligands may be prepared by a variety of methods known in the art such as described, for example, in U.S. Pat. No. 4,769,498, U.S. Pat. No. 4,688,651 and J. Amer. Chem. Soc., 1993, 115, 2066. The organic bidentate phosphite compounds according to the invention can be prepared with the 3- or 3,3'-substituted 2,2'-dihydroxyl-1,1'-binaphthalene bridging compounds. The binaphthol bridging compounds can be prepared by procedures as described in Tetrahedron Lett. 1990, 31(3), 413–416 or in J. Am. Chem. Soc. 1954, 76, 296 and Org. Proc. Prep. International, 1991, 23, 200. The phosphite compounds can be prepared by using the process as described in the earlier mentioned U.S. Pat. No. 5,235,113 to couple these binaphthol bridging compounds with phosphoro-chloridites, $(R^3O)(R^4O)PCl$, prepared by treating $R^3OH$ and/or $R^4OH$ with $PCl_3$.

A more preferred and novel method to prepare the bidentate phosphite ligands which can be used in the process according to the invention is described below.

The phosphorochloridite compound may be prepared by a variety of methods known in the art such as described, for example, in Polymer, 1992, 33, 161; Inorganic Syntheses, 1966, 8, 68; U.S. Pat. No. 5,210,260; Z. Anorg. Allg. Chem., 1986, 535, 221. With bulky ortho-substituted phenols (e.g., 2-tert-butylphenol), phosphorochloridites can be prepared in situ from $PCl_3$ and the corresponding phenol. When preparing bidentate phosphite ligands having terminal $R^3$ or $R^4$ groups which impart a minor steric hinderance, for example when $R^3$ or R4 is an unsubstituted phenanthryl (with no substituent on the ortho-position described above), it has been found that the synthetic route described in the above literature is unsatisfactory. The intermediate $(R^3O)(R^4O)PCl$ compound is difficult to obtain by this route in a high yield and in a pure form or cannot be obtained at all.

An improved process for preparing the phosphorochloridite compound comprises treatment of N,N-dialkyl diarylphosphoramidite with HCl. It has been found that the ligand can be prepared in a high yield when starting from a N,N-dialkyldiarylphosphoramidite, $(R^{11})_2NP(R^3O)(R^4O)$, where $R^{11}$ is an $C_1$–$C_4$ alkyl group, for example methyl, ethyl, propyl, iso-propyl, butyl, sec-butyl or tert-butyl. The $(R^{11})_2NP(R^3O)(R^4O)$ compound can be obtained by reacting $R^3OH$, $R^4OH$ with $(R^{11})_2NPCl_2$. Reacting the $(R^{11})_2NP(R^3O)(R^4O)$ with HCl dissolved in an apolar solvent, for example diethylether, dioxane, or toluene, or with HCl gas gives $(R^3O)(R^4O)PCl$.

N,N-dialkyl diarylphosphoramidites may be prepared by methods known in the art such as described, for example, in Tetrahedron Letters, 1993, 34, 6451; Synthesis, 1988, 2, 142–144 and Aust. J. Chem., 1991, 44, 233.

By contacting the thus obtained $(R^3O)(R^4O)PCl$ with a 3- or 3,3'-substituted, 2,2'-dihydroxy-1,1'-binaphthalene bridging compound, for example by the method described in the above-mentioned U.S. Pat. No. 5,235,113, a bidentate phosphite ligand is obtained which can be used in the process according to the invention.

The catalyst system used in the process according to this invention can be prepared by mixing a suitable rhodium or iridium compound with the phosphite ligand, optionally in a suitable solvent, in accordance with well-known complex-forming methods. The solvent will generally be the solvent used in the hydroformylation. Suitable rhodium and iridium compounds are for example hydrides, halides, organic acid salts, acetylacetonates, inorganic acid salts, oxides, carbonyl compounds and amine compounds of these metals. Examples of suitable catalyst precursors are, for example, $Ir(CO)_2(acac)$, $Ir_4(CO)_{12}$, $RhCl_3$, $Rh(NO_3)_3$, $Rh(OAc)_3$, $Rh_2O_3$, $Rh(acac)(CO)_2$, $Rh(CO)_2(DPM)$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$, (wherein "acac" is an acetylacetonate group; "Ac" is an acetyl group; "COD" is 1,5-cyclooctadiene; and "Ph" is a phenyl group, DPM is 2,2,6,6-tetramethyl-3,5-heptanedionategroup). However, it should be noted that the rhodium and iridium compounds are not necessarily limited to the above listed compounds.

The metal is preferably rhodium.

The ethylenically unsaturated organic compound has at least one "C=C" bond in the molecule and preferably 2 to 20 carbon atoms. Examples of suitable ethylenically unsaturated organic compound are linear terminal olefinic hydrocarbons, for example ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons, for example isobutene and 2-methyl-1-butene; linear internal olefinic hydrocarbons, for example cis- and trans-2-butene, cis- and trans-2-hexene, cis- and trans-3-hexene, cis- and trans-2-octene and cis- and trans-3-octene; branched internal olefinic hydrocarbons, for example 2,3-dimethyl-2-butene, 2-methyl-2-butene and 2-methyl-2-pentene; terminal olefinic hydrocarbon-internal olefinic hydrocarbon mixtures, for example octenes prepared by dimerization of butenes, olefin oligomer isomer mixtures from dimer to tetramer of lower olefins including propylene, n-butene, isobutene or the like; and cycloaliphatic olefinic hydrocarbons for example cyclopentene, cyclohexene, 1-methylcyclohexene, cyclooctene and limonene.

Examples of suitable olefinic compounds include olefinic compounds containing an aromatic substituent such as styrene, alpha-methylstyrene and allylbenzene; and diene compounds such as 1,3-butadiene, 1,5-hexadiene, 1,7-octadiene and norbornadiene. It has been found that with the process according to this invention it is possible to prepare 3-pentenal in moderate yield starting from 1,3-butadiene.

The ethylenically unsaturated organic compound can be substututed with one or more functional groups containing a heteroatom, for example oxygen, sulfur, nitrogen or phosphorus. Examples of heteroatom substituted ethylenically unsaturated organic compounds include vinyl methyl ether, methyl oleate, oleyl alcohol, methyl 2-pentenoate, methyl 3-pentenoate, methyl 4-pentenoate, 3-pentenoic acid, 4-pentenoic acid, 3-pentenenitrile, 4-pentenenitrile, 2-pentenal, 3-pentenal, 4-pentenal, 4-hydroxy-1,7-octadiene, 1-hydroxy-3,7-octadiene, 1-methoxy- 3,7-octadiene, 7-octen-1-al, acrylonitrile, acrylic acid esters, methylacrylate, methacrylic acid esters, methylmethacrylate, vinyl acetate and 1-acetoxy-3,7-octadiene.

The invention is especially directed to hydroformylation processes in which a terminal aldehyde compound is prepared starting from an internally unsaturated organic compound having 4 to 20 carbon atoms. Example of these compounds are described above. Especially internally unsaturated compounds according to:

$$CH_3-CR^{12}=CR^{13}-R^{14} \qquad (7)$$

are used as starting compound, in which $R^{12}$ and $R^{13}$ is an organic group or preferably hydrogen and $R^{14}$ is a $C_1$–$C_{17}$ organic group optionally substituted with one or more functional groups containing a heteroatom, for example oxygen, sulfur, nitrogen or phosphorus. The invention is especially directed at functional compounds with 6 to 20 carbon atoms according to formula (7) in which $R^{12}$ and $R^{13}$ are hydrogen.

A special class of internally unsaturated organic compounds according to formula (7) are 3-pentenenitrile, 3-pentenoic acid and $C_1$–$C_6$ alkyl 3-pentenoate ester compounds. The terminal aldehydes compound prepared by this process starting from these compounds can advantageously be used in the preparation of ε-caprolactam or adipic acid, which are precursors for respectively Nylon-6 and Nylon-6,6. Examples of $C_1$–$C_6$ alkyl 3-pentenoates are methyl-, ethyl-, propyl-, isopropyl-, tert-butyl-, pentyl- and cyclohexyl-3-pentenoate. Methyl and ethyl 3-pentenoate esters are preferred because they are more readily available. The 3-pentenenitrile, 3-pentenoic acid and $C_1$–$C_6$ alkyl 3-pentenoate ester compounds may be present in mixtures containing respectively: 2- and 4-pentenenitrile; 2- and 4-pentenoic acid; and $C_1$–$C_6$ alkyl 2- and 4-pentenoate ester compounds.

The hydroformylation process according to the invention can be performed as described below. The reaction conditions of the hydroformylation process according to this invention are in general the same as used in a conventional process, described for example in U.S. Pat. No. 4,769,498, and will be dependent on the particular starting ethylenically unsaturated organic compound. For example, the temperature can be from room temperature to 200° C., preferably from about 50° to 150° C.

The pressure may vary from atmospheric pressure (0.1 MPa) to 20 MPa, preferably from 0.15 to 10 MPa and more preferably from 0.2 to 1 MPa. The pressure is generally equal to the combined hydrogen and carbon monoxide partial pressure. Extra inert gasses may however be present. The molar ratio hydrogen: carbon monoxide is generally between 10:1 and 1:10 and preferably between 6:1 and 1:2.

The amount of rhodium or iridium (compound) is not specially limited, but is optionally selected so that favorable results can be obtained with respect to catalyst activity and process economics. In general, the concentration of rhodium or iridium in the reaction medium is between 10 and 10,000 ppm and more preferably between 50–1000 ppm, calculated as free metal.

The molar ratio of bidentate phosphite ligand to rhodium or iridium is not specially limited, but is optionally selected so that favorable results can be obtained with respect to catalyst activity and aldehyde selectivity. This ratio generally is from about 0.5 to 100 and preferably from 1 to 10 (mol ligand/mol metal).

The choice of solvent is not critical provided the solvent is not detrimental to catalyst, reactant, and/or product. The solvent may be the mixture of reactants, such as the starting unsaturated compound, the aldehyde product and/or by-products. Suitable solvents include saturated hydrocarbons, for example kerosene, mineral oil or cyclohexane, ethers, for example diphenyl ether tetrahydrofuran or a polyethyleneglycol, for example Carbowax™-400, ketones, for example methyl ethyl ketone or cyclohexanone, nitrites, for example 2-methylglutaronitrile or benzonitrile, aromatics, for example toluene, benzene or xylene, esters, for example methyl valerate or caprolactone, Texanol® (Union Carbide), or dimethylformamide, sulfones (for example tetramethylenesulfone).

The invention is also directed to a catalyst composition comprising the bidentate phopshite described above and rhodium or iridium and its use as hydroformylation catalyst.

The following non-limiting examples further illustrate the present invention.

EXAMPLE 1

Preparation of Ligand 1 a. Esterification of 3-hydroxy-2-naphthoic acid from J. Am. Chem. Soc. 76 (1954) 296

633.65 g (3.34 mol) 3-hydroxy-2-naphthoic acid (Aldrich) and 38 ml $H_2SO_4$ were refluxed in 1200 ml methanol for 7 hours. The reaction mixture was cooled overnight. The precipitated yellow crystals were filtered of, dissolved in diethyl ether, washed with a $NaHCO_3$ solution in water and then washed with water. After drying with $MgSO_4$ and filtration the diethyl ether was removed under vacuo. The residue was recrystallized from methanol yielding 460 g (68%) product. A second crop can be obtained by concentrating the mother liquor.

b. Synthesis of dimethyl 2,2'-dihydroxy-1,1'binaphthalene-3,3-dicarboxylate from OPPI Briefs, 23 (1991) 200

The reaction was performed under $N_2$ atmosphere. To a vigorously stirred solution of methyl 3-hydroxy-2-naphthoate (100 g) and copper(II)chloride (anhydrous) (133 g) in 3000 ml methanol, 289.1 g tert-butylamine was added over a period of 5 min. After the addition was complete the green brown suspension was heated to 50° C. for 20 hours. Then the reaction mixture as cooled to 10° C. and decomposed with 1000 ml 6N HCl. When recooled to 10° C. a lemon-yellow precipitate was formed, which was collected by filtration. After washing with water and a saturated $NaHCO_3$ solution and then dried over $MgSO_4$. Evaporation of the solvent gave a dirty yellow solid which over boiling in methanol for 5 min was cooled to 0° C. and collected. Yield 77 gram (77%).

c. Preparation of di(2-isopropylphenyl)-phosphorochloridite:

The following reaction and product isolation was performed under a dry nitrogen atmosphere. Phosphorus trichloride was distilled prior to use and triethylamine was dried by distillation from calcium hydride. 2-Isopropylphenol(30 g) was dissolved in dry toluene (50 mL) and added dropwise over a one hour period to a vigorously stirred solution of phosphorus trichloride (15.0 g) and triethylamine (24 g) in dry toluene (200 mL) at ambient temperature. The resulting mixture was stirred for another hour and the triethylammoniumchloride salt was removed by filtration. After removing the solvent under vacuum, the residue was distilled to give 70% di(2-isopropylphenyl)-phosphorochlorodite (bp: 166° C., 0.5 mm Hg) with a purity of 90% by $^{31}P$ NMR.

d. Preparation of the final phosphite:

A solution of 4.02 g dimethyl-2,2'-dihydroxy-1,1'-binaphthalene-3,3'-dicarboxylate (as prepared above) in 100 ml toluene was dried by azeotropic distillation. To this solution was added 7.65 g of the di(2-isopropylphenyl) phosphorochloridite from above, 3.6 g triethylamine in 50 mL of toluene. After stirring for one hour at 40° C., the mixture was filtered and the solvent removed in vacuo. The residue was crystallized from n-hexane. Yields of 50–75% of Ligand 1 were obtained.

EXAMPLE 2

Preparation of Ligand 2

A solution of N,N-diethyl di(9-phenanthryl) phosphoroamidite ($^{31}P$ NMR:138.7 ppm) was prepared by adding 2.3 g of triethylamine and 1.74 g (10 mmol) of $Et_2NPCl_2$ at 20° C. to 3.88 g (20 mmol) of 9-phenanthrol in 250 mL of toluene (dried by azeotropic distillation) (Et= ethyl). This solution was reacted with 11 mL of 1M HCl in diethyl ether to give the di(9-phenanthryl) phosphorochloridite ($^{31}P$ NMR:161.4 ppm). The mixture was filtered then 3 g (30 mmol) of triethylamine and 1.98 g of dimethyl 2,2'-dihydroxy-1,1'-binaphthalene-3,3'-dicarboxylate were added. The mixture was stirred for 10 minutes, filtered, solvent evaporated, and the product crystallized from acetonitrile/toluene ($^{31}P$ NMR:126.6 ppm). A yield of 90% of Ligand 2 was obtained.

COMPARATIVE EXPERIMENT 3

Attempt at Preparing Ligand 2 according to the route exemplified in Example 1. An attempt at preparing di(9-phenanthryl)phosphorochloridite from the direct reaction between phosphorus trichloride, two equivalents of 9-phenanthranol and two equivalents of triethylamine failed following a similar procedure described in Example 1. Tri(9-phenanthryl)phosphite was the major product and only about 5% of the desired di(9-phenanthryl) phosphorochloridite was obtained.

EXAMPLE 4

Hydroformylation with Ligand 1

A 25 mL glass lined pressure vessel was charged with 5 mL of a solution containing 11.4 g (100 mmol) methyl-3-pentenoate, 0.068 g (0.2 mmol) of dicarbonyl (2,2,6,6-tetramethyl-3,5-heptanedionato)-rhodium, 1.0 g (1.0 mmol) of Ligand 1 and 1.00 g of tetradecane (internal GC standard) in 100 mL toluene. The ratio of ligand to Rh was 5. The pressure vessel was freed from air by purging first with nitrogen (twice) and then with 1:1 $CO/H_2$ (twice). The vessel was then pressurized to 0.5 MPa. 1/1 $CO/H_2$ and heated to 100° C. with agitation for 2 hours. The heat was shut off and the pressure vessel was allowed to cool to room temperature. The excess gases were vented and the products were analyzed by gas chromatography on a 30M DB-Wax™ capillary GC column. The results are shown in Table 1:

Table 1
M3P Conversion ("Conv")[1] 66.4
% Selectivity to M5FV ("Sel")[2] 82.3
% Selectivity to Methylvalerate ("Redn") 4.0
% Selectivity to M2P ("Isom")[3] 7.6
% Linearity ("Lin")[4] 93.2%
1: M3P and M4P are methyl 3- or 4-pentenoate respectively; Percent M3P and M4P reacted.
2: M5FV=methyl-5-formylvalerate; selectivity is (mole M5FV/(mole M3P+M4P converted). The conversion of M3P to M4P is not regarded as conversion of starting compound because M4P is considered an equivalent starting compound.
3: M2P=Methyl-2-pentenoate; "isom"=moles M2P formed/ moles(M3P+M4P) converted.
4: Calculated as 100* M5FV/(M5FV+branched formylvalerates).

The example illustrates the very high selectivity to linear aldehyde from an internal functionalized olefin that may be obtained with the catalyst of this invention.

EXAMPLE 5

Hydroformyalation using Ligand 2

A 150 mL Hastelloy-C autoclave (Parr) was filled under nitrogen with 5.8 mg dicarbonyl(2,2,6,6-tetramethyl-3,5-heptanedionato)-rhodium ($4.8 \times 10^{-5}$ mol), $14.0 \times 10^{-5}$ mol Ligand 2 (ligand/rhodium ration (L/Rh)=2.9 mol/mol) and 60 mL of toluene. The autoclave was closed and purged with nitrogen. The autoclave was brought to 1 MPa of carbon monoxide/hydrogen (1:1) and heated to 90° C. over a ca. 30 min. period. At 90° C. and 1 MPa, a solution of 7.44 g (65 mmol) freshly distilled methyl 3-pentenoate and 1.2 gram nonane diluted to 15 mL with toluene was then injected into the autoclave. The reaction was run for 7 hours, after which the reaction was cooled and analyzed. GC analyses showed 90.1% Conv.; 75.1% Sel.; 5.7% Redn.; 90.3% Lin.

EXAMPLES 6–9 AND COMPARATIVE EXPERIMENT 10

Hydroformylation using Ligands 3–6

Example 4 was repeated (100° C., 0.5 MPa 1:1 $CO/H_2$ pressure, a ligand/Rhodium ratio of 5/1 (mole/mole), 200 ppm Rh as dicarbonyl(2,2,6,6-tetramethyl-3,5-heptanedionato)rhodium, and 1 molar M3P in toluene) at a reaction time of 2 hours in which the ligand had the following general formula:

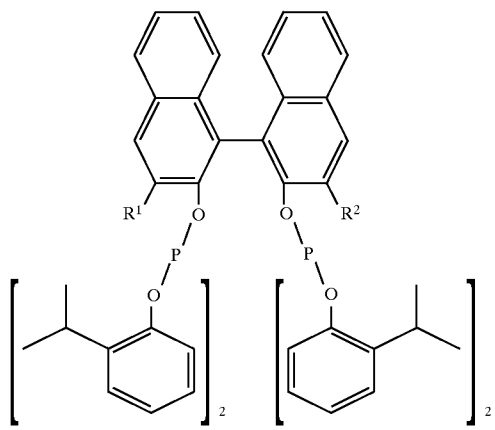

(8)

The results are summarized in Table 2.

TABLE 2

| Example | Ligand | $R^1$ | $R^2$ | Conv | Redn | Sel | Lin |
|---|---|---|---|---|---|---|---|
| 6 | 3 | $CO_2$i-Pr | $CO_2$i-Pr | 53 | 4 | 85 | 94 |
| 7 | 4 | $CH_3$ | $CH_3$ | 36 | 5 | 75 | 93 |
| 8 | 5 | $C_2H_5$ | $C_2H_5$ | 36 | 5 | 75 | 92 |
| 9 | 6 | $C_2H_5$ | H | 23 | 4 | 74 | 88 |
| Comp. 10 | | H | H | 70 | 9 | 66 | 82 |

Comparative Experiment 10 shows that the ligand without substituents on the 3,3' position of the bisnaphthol bridge gives significantly lower selectivity to the linear aldehyde

EXAMPLES 11–14

Hydroformylation using Ligands 8–11

The hydroformylation conditions for Example 4 was used with ligands according to the following general formula:

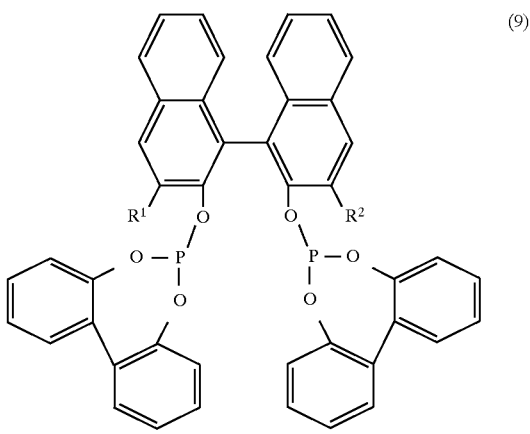

(9)

The results are presented in Table 3:

TABLE 3

| Example | Ligand | R$^1$ | R$^2$ | Conv | Redn | Sel | Lin |
|---|---|---|---|---|---|---|---|
| 11 | 8 | CO$_2$Et | CO$_2$Et | 99 | 11 | 64 | 77 |
| 12 | 9 | SiPh$_3$ | SiPh$_3$ | 73 | 23 | 64 | 97 |
| 13 | 10 | CO$_2$i-Pr | CO$_2$i-Pr | 91 | 8 | 63 | 78 |
| 14 | 11 | CO$_2$Me | CO$_2$Me | 98 | 9 | 61 | 72 |

EXAMPLE 15a AND 15b

Hydroformylation with Ligands 12 and 13

Hydroformylation reactions were performed using the procedure of Example 4 with Ligands 12 and 13. The results are shown in Table 4.

TABLE 4

| Example | Ligand | Conv | Redn | Sel | Lin |
|---|---|---|---|---|---|
| 15a | 12 | 82.2 | 6.7 | 55.0 | 70.0 |
| 15b | 13 | 16.0 | 2.0 | 51.7 | 69.3 |

EXAMPLE 16 AND 17 AND COMPARATIVE EXPERIMENT 17b

Hydroformylation of Hexene-1 and Hexene-2 with Ligand 1 and with Ligand C

The experiment in Example 4 was repeated except that the methyl-3-pentenoate was replaced by an equivalent amount of hexene-1 or hexene-2 and the CO/H$_2$ pressure at temperature (100° C.) was 0.68 MPa and the reaction was allowed to run for 4 hours. Ligand 1 was used and for comparison tetrakis(di-(2,4-di-tert-butylphenyl)phosphito)-pentaerythritol (Ligand C) was used. Analysis of the products gave the results shown in Table 5.

TABLE 5

| Example | Ligand | Substrate | Conv. to aldehydes[1] | Lin. Lin. |
|---|---|---|---|---|
| 16 | 1 | Hexene-1 | 73.4 | 98.7 |
| 17 | 1 | Hexene-2 | 50.4 | 97.3 |
| Comp. 17a | C | Hexene-2 | 10.3 | 95.8 |

[1]Moles of linear and branched aldehydes formed per mole hexene charged to the reactor; unreacted hexenes were not measured. The results demonstrate that very high linear selectivity can be obtained with unfunctionalized terminal and internal olefins.

The prior art phosphite (Ligand C) shows much lower activity when starting from internal olefins.

EXAMPLES 18 AND 19

Hydroformylation of 3-Pentenenitrile with Ligands 1 and 14

Example 18

The experiment in Example 4 was repeated except that the methyl-3-pentenoate was replaced by an equivalent amount of 3-pentenenitrile and the ligand was Ligand 1. Analysis of the products showed a mixture of 3-, 4-, and-formylvaleronitriles (hydroformylation products) and valeronitrile (VN; reduction product). The results are summarized in Table 6.

Example 19

The experiment in Example 4 was repeated except that the methyl-3-pentenoate was replaced by an equivalent amount of 3-pentenenitrile and the ligand was the Ligand 14. Analysis of the producs gave the results shown in Table 6.

TABLE 6

| Example | Ligand | Conv | Redn* | Sel** | Lin |
|---|---|---|---|---|---|
| 18 | 1 | 85.2 | 21.0 | 42.7 | 54.4 |
| 19 | 14 | 37.4 | 16.3 | 44.6 | 55.6 |

*The reduction product was valeronitrile
**Selectivity to 5-formylvaleronitrile

The results show that moderately high selectivity to the linear 5-formylvaleronitrile (5FVN; a caprolactam precursor) can be obtained with the catalysts of this invention.

EXAMPLES 20, 21

Hydroformylation of Butadiene with Ligands 8 and 10

The experiment in example 4 was repeated except that the methyl-3-pentenoate was replaced by an equivalent amount of 1,3-butadiene, the solvent was tetrahydrofuran, the temperature was 90° C., the CO/H$_2$ total pressure at 90° C. was 6.8 MPa and the ligand was either Ligand 8 or 10 and the ligand/Rh ratio was 3. Analysis of the products showed a mixture of pentenals (primarily trans-3-pentenal), pentanal (reduction product) and dialdehydes (primarily 1,4-butanedial). The results are summarized in Table 6.

TABLE 6

| Example | Ligand | Conv | Pentanal | 3-Pentanals | Dials |
|---|---|---|---|---|---|
| 20 | 8 | 76.7 | 2.8 | 45.2 | 7.1 |
| 21 | 10 | 66.7 | 2.1 | 29.2 | 5.0 |

EXAMPLES 22–27

Hydroformylation of Methyl 3-pentenoate using Ligands 15–19 and 7

A 150 mL Hastelloy-C autoclave (Parr) was filled under nitrogen with 5.8 mg dicarbonyl(2,2,6,6-tetramethyl-3,5-heptanedionato)-rhodium (4.8×10$^{-5}$ mol), 60 mL of toluene, and a ligand selected from Ligands 15–19 and 7 (ligand/rhodium molar ratio (L/Rh) varied from 2.2 to 3.1). The autoclave was closed and purged with nitrogen. The autoclave was brought to 1 MPa of carbon monoxide/hydrogen (1:1) and heated to 90° C. over a ca. 30 min. period. At 90° C. and 1 MPa, a solution of 7.44 g (65 mmol) freshly distilled methyl 3-pentenoate and 1.2 gram nonane diluted to 15 mL with toluene was then injected into the autoclave. The reaction times are listed in Table 7. Product analyses were done by GC and the results are summarized in Table 7.

TABLE 7

| Example | Ligand | L/Rh[1] | Time (hrs) | Conv (%) | Sel (%) | Redn (%) | Lin (%) |
|---|---|---|---|---|---|---|---|
| 22 | 15 | 3.1 | 7 | 81.8 | 84.6 | 3.9 | 94.9 |
| 23 | 16 | 3.1 | 6 | 77.1 | 72.9 | 2.6 | 79.6 |
| 24 | 17 | 2.2 | 8 | 84.2 | 79.2 | 4.0 | 93.2 |
| 25 | 18 | 2.9 | 6 | 87.3 | 81.2 | 4.7 | 92.3 |

TABLE 7-continued

| Example | Ligand | L/Rh[1] | Time (hrs) | Conv (%) | Sel (%) | Redn (%) | Lin (%) |
|---|---|---|---|---|---|---|---|
| 26 | 19 | 2.2 | 21 | 69.5 | 82.0 | 3.6 | 94.6 |
| 27 | 7 | 2.2 | 18.5 | 84.0 | 81.0 | 4.4 | 94.5 |

[1]Ligand/rhodium molar ratio.

Example 28

Example 22 was repeated using Ligand 15 and a ligand/rhodium ratio of 3. As substrate cis 2-butene was used. The total pressure was 2 MPa. After 4 hours a conversion of 66.2% with 98% selectivity for pentanal and a linearity of 98% were obtained.

Examples 29–37

Example 4 was repeated except that a different ligand was used. See Table 9 ligand choice and results.

TABLE 9

| Ex. | Ligand No. | Conv. | Sel. | Lin. |
|---|---|---|---|---|
| 29 | 20 | 73.0 | 84.9 | 96.0 |
| 30 | 21 | 53.1 | 84.5 | 93.6 |
| 31 | 22 | 88.1 | 83.4 | 95.8 |
| 32 | 23 | 88.0 | 83.4 | 94.5 |
| 33 | 24 | 91.5 | 83.3 | 93.6 |
| 34 | 25 | 94.8 | 83.2 | 97.9 |
| 35 | 26 | 97.5 | 82.2 | 97.4 |
| 36 | 27 | 53.4 | 80.8 | 91.3 |
| 37 | 28 | 56.3 | 80.1 | 89.8 |

Example 38–44

Example 18 was repeated except that a different ligand was used. See Table 10 for ligand choice and results.

TABLE 10

| Ex. | Ligand No. | Conv. | Sel. | Lin. |
|---|---|---|---|---|
| 38 | 15 | 99 | 65..6 | 78.1 |
| 39* | 15 | 59 | 67.3 | 87.9 |
| 40 | 25 | 99 | 73.7 | 83.8 |
| 41** | 25 | 94 | 69.7 | 79.6 |
| 42 | 26 | 99 | 72.1 | 85.8 |
| 43** | 26 | 91 | 73.9 | 82.6 |
| 44 | 20 | 82 | 53.1 | 64.3 |

*The feed gas was 35% CO and 65% $H_2$
**The feed gas was 65% CO and 35% $H_2$

Example 45

A Hastalloy B autoclave with a volume of 1 liter was loaded with a 200 g catalyst solution. The catalyst solution consisted of: 568 g m-xylene, 1.105 g (4.3) mmol) rhodium dicarbonyl acetylacetonate (Rh(acac)(CO)$_2$), 20.0 g (65.8 mmol) tri-(ortho-tolyl)phosphine and 14.0 g (12.8 mmol) of a bidentate phosphite ligand (mw=1090) with formula (10)

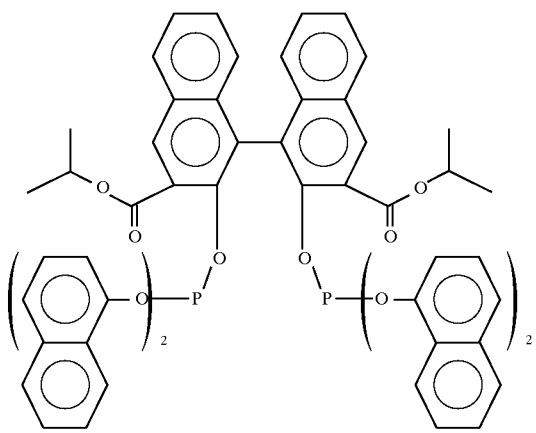

Ton the autoclave (the reactor) was also added 300 g of methol-3-pentenoate (M3P). The reactor was heated under 1 MPa CO/$H_2$ pressure (1:1 mol/mol CO/$H_2$) to 95° C. The CO/$H_2$ was constantly fed to the reactor in such a way that there was always an off-gas stream from the reactor. The reactor could contain approximately 500 ml liquid. As soon as the reactor contained more than approximately 500 ml, it overflowed via a dip tube and the excess of reaction mixture was continuously removed from the reactor. The reactor effluent stream existing of liquid in excess of 500 ml and unreacted gases was let down to atmospheric pressure via a back pressure regulator and fed into a gas/liquid separator. The gas was -after passing through a condenser to remove condensables- vented to 1 bar. The stream collected in the bottom of the gas/liquid separator was fed through a control valve to a first short path rolled film evaporator. In this evaporator most of the unreacted M3P, light by-products and a small part of the aldehyde products were evaporated under vacuum (600 mm Hg at 90° C. wall temperature). The liquid residue (bottom stream) was passed through a column filled with an amount of 7 g of a weakly basic Amberlist A21 resin. From there it was pumped to a second short path rolled film evaporator. In this evaporator the remainder of the unreacted M3P and a part of the MFV products were evaporated under a higher vacuum (100 mm Hg at 90° C. heating temperature). The residue of the second evaporator was pumped back into the readtor thereby closing the loop. The temperature and pressure of both evaporators were adjusted such that at a stable running situation: a constant total liquid inventory in the set up, was maintained. (Approx. 1200 ml if calculated back to reactor liquid prior to distillation.)

After 2 hours of reaction at 95° C. fresh M3P was pumped into the reactor at a rate of 90 g/h and also more catalyst solution was pumped in at a rate of 80 g/h. CO and $H_2$ are fed at a flow-rate of 30 Nl/h. The pressure was set at 0,5 MPa. The approx. 4 hours all the distillations and pumps were operating and the catalyst feed is stopped. After another 16 hours the set-up reached a steady state. At the stable point the Rh concentration in the reactor was approximately 300 ppm. The Rh/phosphite molar ratio was 1/3 and the phosphine/phosphite molar ratio was 5/1.

Once every 24 h a liquid sample taken from the gas-liquid separator. This was done very carefully excluding contact with oxygen and moisture using a sample taker which was carefully opened in a dry-box making up the samples for all kinds of analysis. The samples were analyzed for organic and inorganic components using gaschromatography GC, high pressure liquid chromatography (HPLC), nuclear magnetic resonance (NMR) and Elemental analysis. 210 hours into the experiment the composition of the liquid in the reactor was determined as: 0.39 wt. % methyl-4-pentenoate, 0.06 wt. % methyl-cis-2-pentenoate, 1.82 wt. % methol valerate, 9.17 wt. % methyl-trans-3-pentenoate, 2.61 wt. % methyl-cis-3-pentenoate, 4.48 wt. % methyl-trans-2-pentenoate, 0.04 wt. % xylene, 0.48 wt. % methyl-2-formylvalerate, 1.06 wt. % methyl-3-formylvalerate, 1.61 wt. % methyl-4-formylvalerate, 71.89 wt. % methyl-5-formylvalerate (M5FV), 0.23 WT. % monomethyladipate, 0.48 wt. % aldol condensation products, 0.64 wt. % tri (orthotoly)phosphine, 0.44 wt. % tri(ortho-tolyl)phosphine-oxide and 4.6 wt. % of heavies and catalyst components.

To ensure that the substrate is free of hydroperoxides the M3P is batch distilled at atmospheric pressure over triphenylphosphine and fed over a column filled with alumina-oxide prior to feeding it to the reactor. The distillates were continuously collected analyzed for product composition.

The reaction could be run for 250 h without significant phosphite degradation by oxidation. Selectivity to methyl 5-formylvalerate during the run changed from 84 to 82%. The conversion of methyl 3-pentenoate changed a little because of sampling from the set-up going from 79 to 77%. The selectivity to methyl-5-formuylvalerate (M5FV) is calculated as the amount (in mol/h) of M3P which has been converted to M5FV divided by the amount (in mol/h) of M3P which has reacted.

Example 46

Example 45 was repeated, except that the feed methyl-3-pentenoate (M3P) was replaced by a mixture consisting of 91.8 w % methyl-3-pentenoate and 8.2 w % methyl-trans-2-pentenoate. In this experiment the reaction could be run for 190 hours at a degree of M3P conversion of 77% at a selectivity of 85.2% to methyl-5-formyl-valerate (M5FV). The selectivity was calculated (based on M3P) as in Example 42.

This high selectivity is surprising because batch experiments starting with M2P as feed indicated a much lower selectivity to M5FV (about 7%) as was described in patent EP-A-556681, Example 16.

Examples 45 and 46 demonstrate that the present catalyst system is stable over a prolonged period of time. The process using such catalyst system is clearly capable of being performed continuously, i.e. a continuous process.

What is claimed is:

1. A hydroformylation catalyst composition comprising rhodium and a bidentate organic phosphite ligand having the structure:

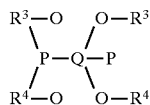 (1)

in which the two phosphorus atoms of the phopshite ligand are linked with a 2,2'-dihydroxyl-1,1'-binapthalene bridging group having the following structure (Q):

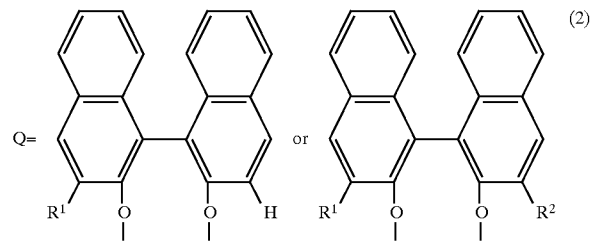

in which $R^1$ and $R^2$ are substituents other than hydrogen and in which $R^3$ and $R^4$ are the same or different substituted monovalent aryl groups and/or any one of $OR^3$ and $OR^4$ connected to one phosphorus atom forms an —O—$R^5$—O—group, where $R^5$ is a divalent organic group containing one or two aryl groups.

2. A hydroformylation catalyst composition according to claim 1, wherein $R^1$ and $R^2$ are individually selected from the group of alkyl, aryl, triarylsilyl, trialkylsilyl, carboalkoxy, carboaryloxy, aryloxy, alkoxy, alkylcarbonyl, arylcarbonyl, oxazole, amide, amine or a nitrile.

3. A hydroformylation catalyst composition according to claim 2, wherein $R^3$ and $R^4$ are the same or different substituted monovalent $C_6$–$C_{20}$ aryl groups containing at least one $R^6$ group in the ortho position relative to the oxygen atom, where $R^6$ is $C_1$–$C_{20}$ alkyl or $C_6$–$C_{20}$ aryl or $R^3$ and $R^4$ are monovalent $C_{10}$–$C_{20}$ aromatic fused ring systems with 2 or more rings.

4. A hydroformylation catalyst composition according to claim 3, wherein $R^1$ and $R^2$ are carboalkoxyl groups, having the formula —$CO_2R$, in which R is a $C_1$–$C_{20}$alkyl or a $C_6$–$C_{12}$aryl group.

5. A hydroformylation catalyst composition according to claim 3 or 4, wherein $R^3$ and $R^4$ are phenyl groups, in which $R^6$ is a $C_1$–$C_6$ alkyl group.

6. A hydroformylation catalyst composition according to claim 3 or 4, wherein $R^3$ and $R^4$ are 9-phenanthryl or 1-naphthyl groups.

7. A hydroformylation catalyst composition according to claim 3 or 4 wherein $R^3$ and $R^4$ are fused aromatic ring systems having 2 to 4 fused rings.

8. A hydroformylation catalyst composition according to claim 3 or 4, wherein $R^3$ and $R^4$ are fused aromatic ring systems having 10 to 20 carbon atoms.

* * * * *

UNITED STATES PATENT AND TRADEMARK OFFICE
CERTIFICATE OF CORRECTION

PATENT NO. : 5,874,641
DATED : February 23, 1999
INVENTOR(S) : BURKE et al.

It is certified that error appears in the above-identified patent and that said Letters Patent is hereby corrected as shown below:

In columns 2, 3 and 25,

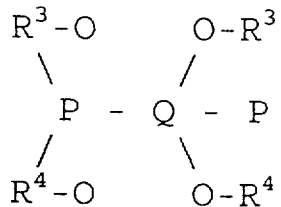

should be:

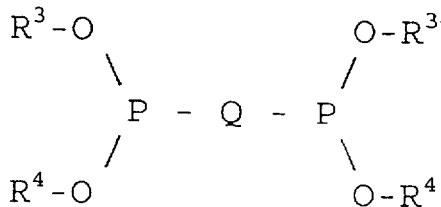

In columns 24, line 19, "Ton the autoclave" should be --To the autoclave-- and in column 24, line 20, "methol-3-pentenoate" should be --methyl-3-pentenoate--.

UNITED STATES PATENT AND TRADEMARK OFFICE
CERTIFICATE OF CORRECTION

PATENT NO.    : 5,874,641

DATED         : February 23, 1999

INVENTOR(S)   : BURKE et al.

It is certified that error appears in the above-identified patent and that said Letters Patent is hereby corrected as shown below:

In column 9, ligands 11 and 12 should be shown as:

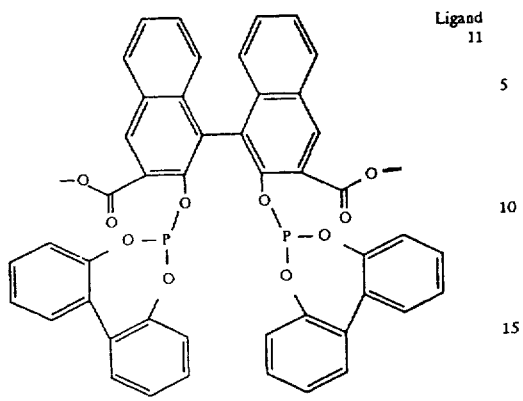

Ligand 11

UNITED STATES PATENT AND TRADEMARK OFFICE
CERTIFICATE OF CORRECTION

PATENT NO.   : 5,874,641
DATED         : February 23, 1999
INVENTOR(S) : BURKE et al.

It is certified that error appears in the above-identified patent and that said Letters Patent is hereby corrected as shown below:

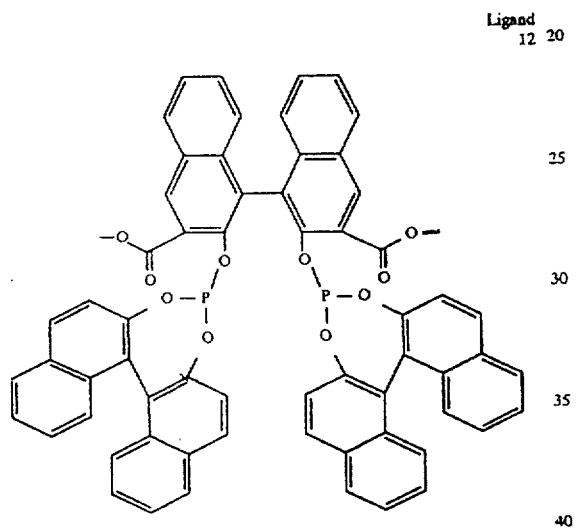

Signed and Sealed this

Thirty-first Day of August, 1999

Attest:

Q. TODD DICKINSON

*Attesting Officer*     *Acting Commissioner of Patents and Trademarks*